United States Patent [19]

Linker, III et al.

[11] Patent Number: 4,834,739
[45] Date of Patent: May 30, 1989

[54] EXTERNAL FEMININE PROTECTION DEVICE WITH SKID-RESISTANT COATING FOR HOLDING THE DEVICE IN PLACE

[75] Inventors: Paul M. Linker, III, Appleton; Ruth A. Lachapell, Menasha, both of Wis.

[73] Assignee: Kimberly-Clark Corporation, Neenah, Wis.

[21] Appl. No.: 134,423

[22] Filed: Dec. 17, 1987

[51] Int. Cl.$^4$ ............................................. A61F 13/16
[52] U.S. Cl. ................................. 604/385.1; 604/386
[58] Field of Search .................. 604/385.1, 385.2, 358, 604/386, 387, 389, 375, 376

[56] References Cited

U.S. PATENT DOCUMENTS

| | | | |
|---|---|---|---|
| 3,283,992 | 11/1966 | Hanson et al. | 229/53 |
| 3,294,090 | 12/1966 | Younger. | |
| 3,495,761 | 2/1970 | Turai et al. | 229/53 |
| 3,860,431 | 1/1975 | Payne et al. | 106/36 |
| 3,881,490 | 5/1975 | Whitehead. | |
| 4,136,699 | 1/1979 | Collins et al. | 604/387 |
| 4,217,901 | 8/1980 | Bradstreet et al. | 604/387 |
| 4,285,343 | 8/1981 | McNair | 604/387 |
| 4,389,211 | 6/1983 | Lenaghan | 604/383 |
| 4,421,805 | 1/1983 | Prader | 428/35 |
| 4,460,364 | 7/1984 | Chen et al. | 604/387 |
| 4,488,918 | 12/1984 | Jofs | 156/79 |
| 4,490,148 | 12/1984 | Beckestrom | 604/385 |
| 4,554,191 | 11/1985 | Korpman | 604/387 |
| 4,673,403 | 6/1987 | Lassen | 604/385 |

FOREIGN PATENT DOCUMENTS 0234194 1/1987 European Pat. Off. .
832380 1/1983 South Africa .

Primary Examiner—John D. Yasko
Attorney, Agent, or Firm—Paul A. Leipold; Thomas J. Connelly

[57] ABSTRACT

An absorbent article for absorption of human exudate is disclosed having an absorbent, a bodyside layer, a backing layer and a skid-resistant coating applied to at least one of the layers. The coating has a coefficient of friction of greater than 1 and a Sheffield smoothness rating of greater than about 200 when utilizing a modified ASTM test. The nonadhesive coating facilitates positioning the article relative to the anatomy of a user.

15 Claims, 7 Drawing Sheets

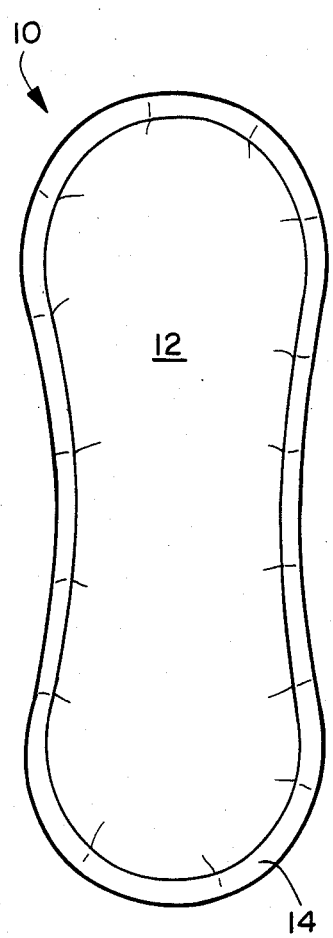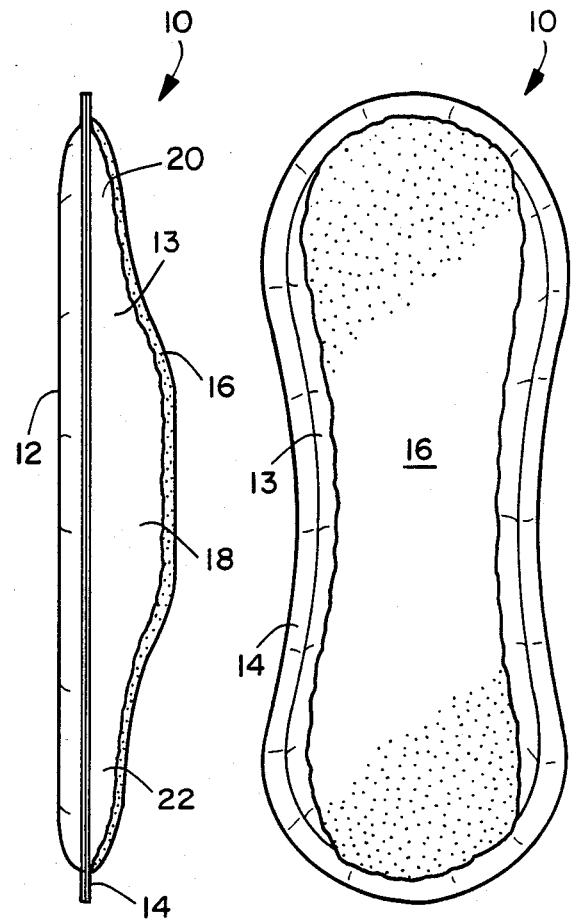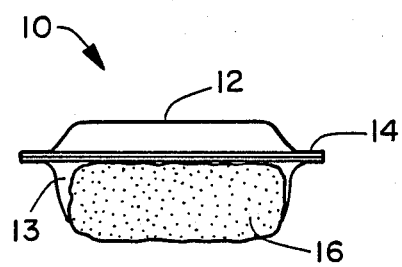
FIG. 1  FIG. 2  FIG. 3
FIG. 4

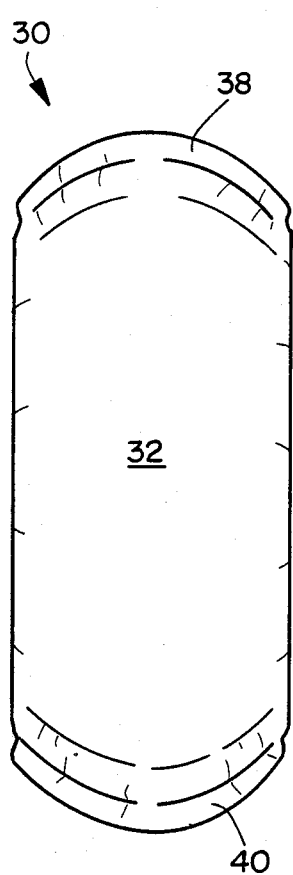 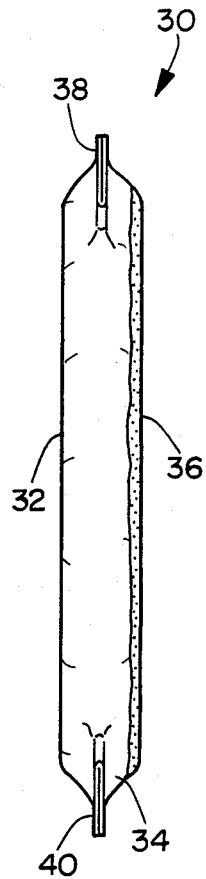 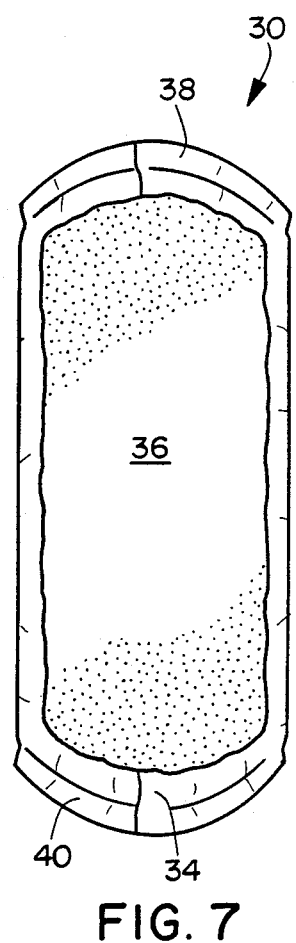
FIG. 5  FIG. 6  FIG. 7
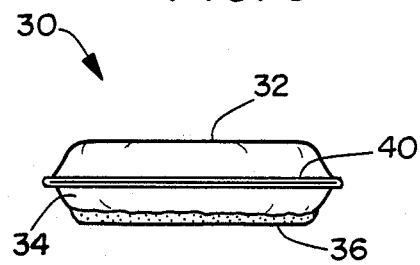
FIG. 8

EXTERNAL FEMININE PROTECTION DEVICE WITH SKID-RESISTANT COATING FOR HOLDING THE DEVICE IN PLACE

FIELD OF THE INVENTION

This invention relates to an absorbent article having a nonadhesive coating for holding the article relative to the anatomy of the user. More particularly, it relates to feminine catamenial pads which use a nonadhesive coating having a high coefficient of friction to hold the pad in pace either against the user's body or to the undergarment.

BACKGROUND OF THE INVENTION

There has been a variety of devices or appliances configured for catamenial devices. Generally there have been offered two basic kinds of feminine protection device. These are sanitary napkins or pads that have been developed for external use, and tampons that have been developed for residence within the vaginal cavity and interruption of menstrual flow therefrom.

The positioning of feminine hygiene devices so as to stay in the proper location and be comfortable and unobtrusive has been of continuing interest in feminine hygiene. The use of pads or feminine napkins held in place by a belt attached to tabs on the feminine napkins was the traditional method of holding pads in place for many years. Now, the majority of external feminine products are held in place against the undergarment of the user by utilization of pressure-sensitive adhesives. Such pressure-sensitive adhesives are placed on the back of a feminine pad and covered by a peel strip that is removed prior to attachment of the pad onto the undergarment of the wearer. The use of such adhesives presents several disadvantages. Among these disadvantages are that the adhesive may stick too firmly to the undergarment and make removal difficult. A second disadvantage is that the adhesive may discolor the undergarment, and a third disadvantage is that the pad may tear apart at the time of removal. Furthermore, the cost of adhesives and the peel strips necessary to cover them is a significant portion of the cost of the feminine pad. Adhesives can also cause discomfort if the feminine pad is inadvertently placed upside down in the undergarment such that the adhesive contacts the body.

Therefore, it would be desirable to make a product which would not require a pressure-sensitive adhesive, but could adequately maintain its position within the undergarment of the wearer and in correct placement on the body.

Other methods of maintaining pads for absorption of human exudate have been proposed. It has been proposed in U.S. Pat. No. 3,881,490 issued to White head et al., that a pad be provided with a polyurethane foam laminated to the backing element of the pad. In U.S. Pat. No. 4,490,148 issued to Beckstrom, an incontinence device is proposed that has a friction-increasing strip fixed to the underside of the garment. And in U.S. Pat. No. 4,389,211 issued to Lenaghan, the use of a velcro material in contact with the foam outer surface of a feminine pad is utilized as a placement mechanism. However, the above materials suffer from the disadvantage that the foam materials are relatively high in cost and require adhesive connection to the undergarments. Further, such materials have not been shown to be particularly preferred by the users of the undergarments to which they are attached. Therefore, there is a continuing need for an improved system for a nonpressure-sensitive adhesive system for holding catamenial devices in place that is low in cost and effective.

SUMMARY OF THE INVENTION

The general object of this invention is to overcome the disadvantages of prior systems of holding pads for human exudate in place.

Another object of this invention is to provide a low cost system for holding garments in place.

Still another object of this invention is to provide a system of holding absorbent articles in place that is unobtrusive.

Still further, an object of this invention is to provide a system of holding absorbent articles in place that will not stain the undergarment.

Other objects and advantages of the present invention will become apparent to one skilled in the art upon reading the following description.

Briefly, the invention relates to an absorbent article, such as a pad, for absorption of human exudate that is provided with a coating having a high coefficient of friction. Among the preferred coatings are materials formed from modified acrylics. The materials preferably have a coefficient of friction of greater than about 1.0 and a Sheffield smoothness rating of greater than 200 when utilizing a modified ASTM test D-1894.

The invention also includes an embodiment whose skid-resistant surface is placed on at least a portion of the bodyside of an absorbent pad to hold it in place.

BRIEF DESCRIPTION OF THE DRAWINGS

FIGS. 1, 2, 3 and 4 are top, side, bottom and end views of a pad in accordance with the invention.

FIGS. 5, 6, 7 and 8 are top, side, bottom and end views of an alternative pad in accordance with the invention.

DETAILED DESCRIPTION OF THE PREFERRED EMBODIMENTS

Figure 9:
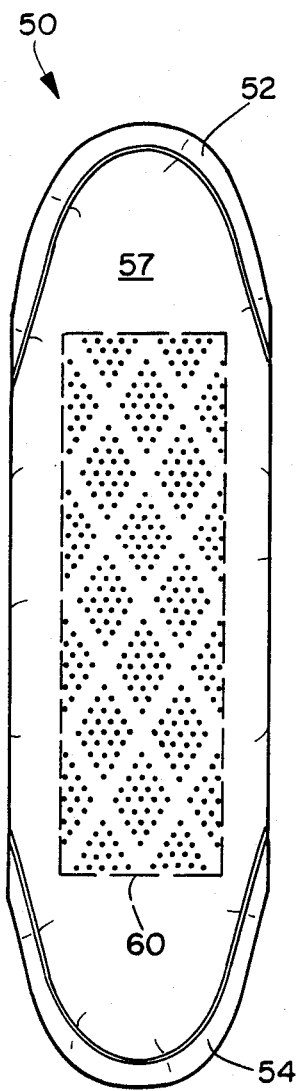
FIGS. 9, 10 and 11 are top, side and bottom views of a pad in accordance with the invention.

The invention as illustrated by the pad of FIGS. 1, 2, 3 and 4 is an hourglass-shaped pad 10 that has a generally planar bodyside surface 12 that has the fluid-impermeable backing member 13 joined to the cover 12 by adhesive connection in the border area 14. The hourglass-shaped pad 10 has a thicker absorbent in the middle 18 than at the ends 20 and 22. Applied to the lower surface of the pad 10 is a skid-resistant coating 16.

FIGS. 5, 6 and 7 illustrate a pad 30 that has a fluid-permeable bodyside member 32 that is wrapped around the pad, overlapped at the bottom 34 and the overlap sealed with adhesive (not shown). The lower portion of the pad is provided with a skid-resistant coating 36. The pad is sealed at the ends 38 and 40 by heat-fusing of the cover material.

Figure 10:
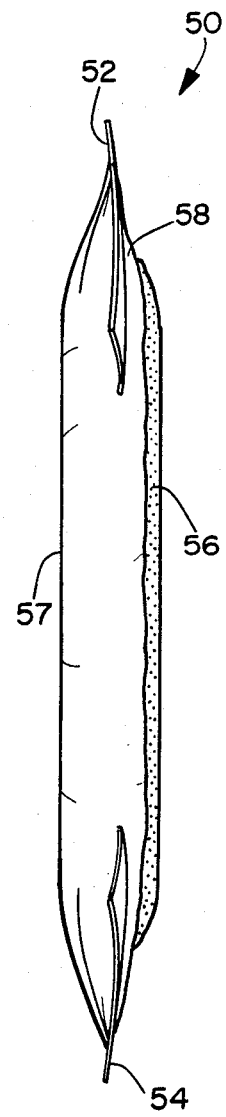
Figure 11:
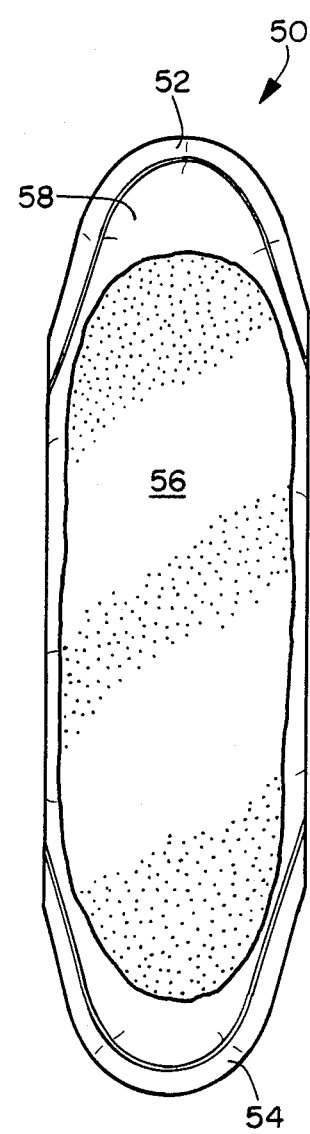
Figures 12, 13:
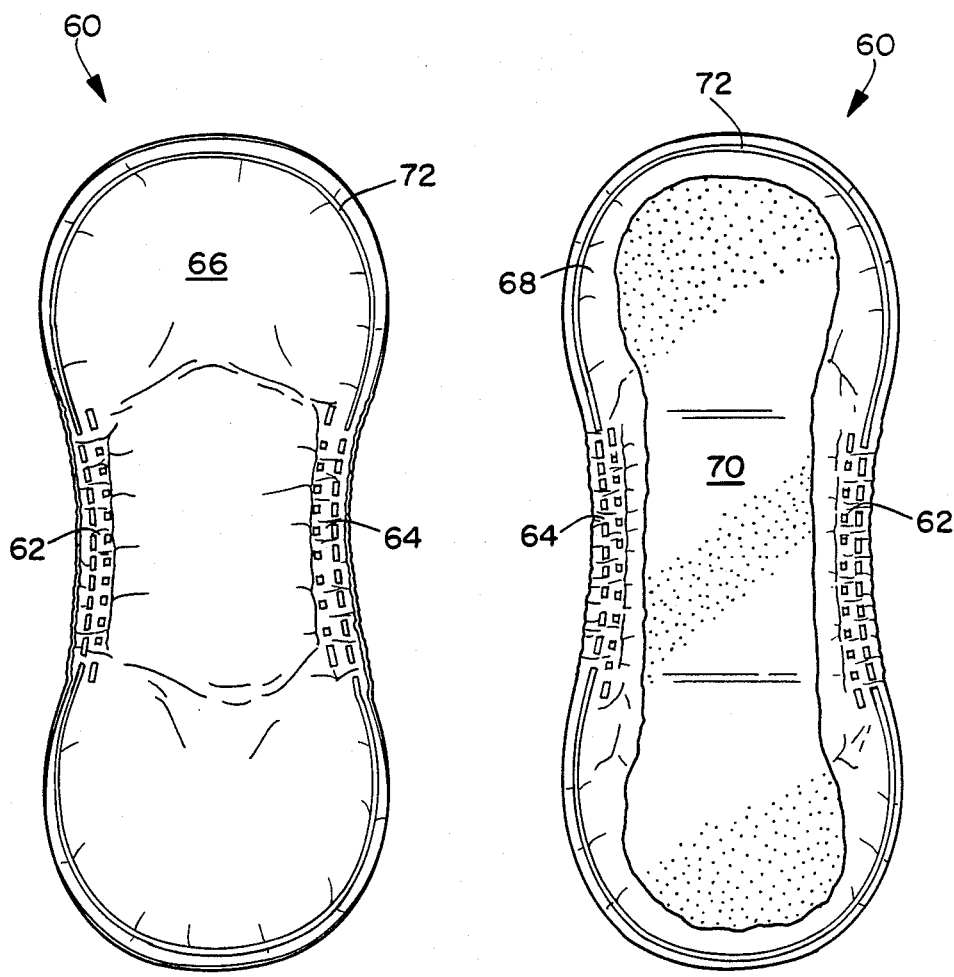
FIGS. 12, 13, 14 and 15 are top, bottom, side and perspective views of a coated pad in accordance with the invention.
Figure 14:
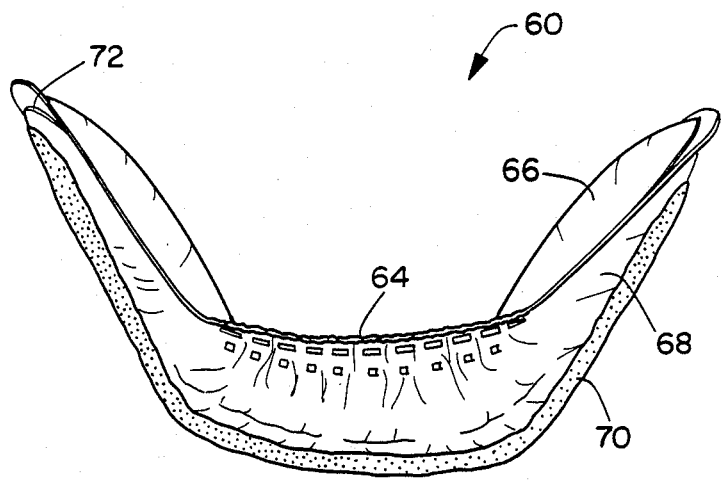
Figure 15:
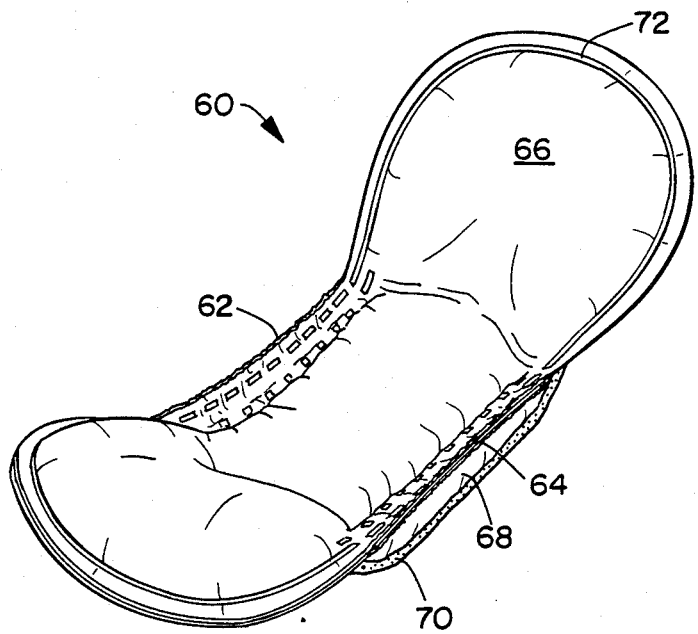

FIGS. 9, 10 and 11 illustrate a pad 50 having rounded ends 52 and 54. The pad 50 is provided with a skid-resistant coating 56. The bodyside or cover of the pad 57 is provided with a perforated area 60 that aids in the flow of material through the fluid-permeable cover 57 to the absorbent (not shown) located in the interior of the pad 50. The coating 56 covers substantially the entire back surface 58 of the pad 50. As used herein, top refers to the bodyside of the pad 57 while back refers to the garment side.

FIGS. 12, 13, 14 and 15 illustrate a shaped pad 60 in accordance with the invention. The shaped pad is provided with gathered areas 63 and 64 at the sides of the pad that are gathered such that the pad 60 curves to better conform to the body. Areas 62 and 64 further raise to form walls to aid in leakage prevention. The pad is provided with a bodyside fluid-permeable member 66 and a fluid-impermeable backing member 68. A skid-resistant surface coating 70 is provided so that the pad 60 will remain in proper location against the wearer's body. The bodyside fluid-permeable member 66 on the top is sealed to the fluid-impermeable backing member 68 at heat seal line 72.

Figure 16:
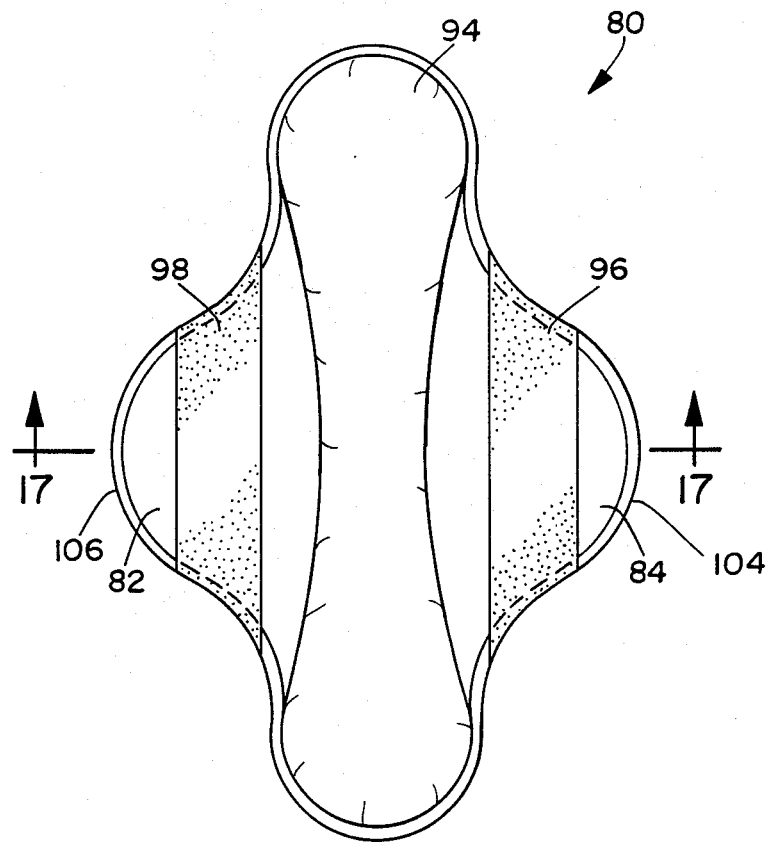
FIGS. 16 and 17 are top and cross-sectional views of another embodiment of the invention.
Figure 17:
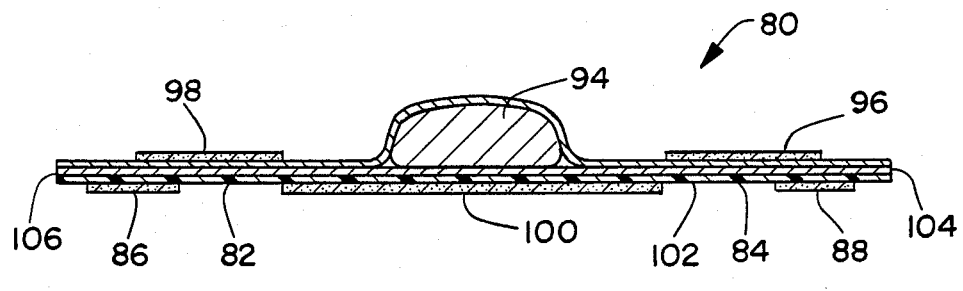

In FIGS. 16 and 17 a pad 80 is shown having wings 82 and 84 that are intended to be sealed by adhesive areas 86 and 88 either to each other or to the wearer's undergarment. The pad 80, best illustrated in FIG. 17, is provided with skid-resistant coatings 96 and 98 that will face the bodyside of the pad 90. When the pad 80 is worn, the coatings 96 and 98 will be located in the groin area of the wearer and prevent movement of the pad 80 by increasing skid resistance against the wearer's body. An absorbent member 94 is illustrated having an hourglass shape. There is also provided a skid-resistant coating 100 on the fluid-impermeable backing 102 of the pad 80. The coating 100 prevents movement of the pad 80 against the wearer's undergarment in order to hold the pad 80 in place in combination with skid-resistant coatings 96 and 98 and the overlapped wings 82 and 84. It is also possible that the pad 80 would not be provided with the adhesive areas 86 and 88 such that the extremeties 104 and 106 of the wings 82 and 84 will hang from the edge of the crotch of the undergarment against the user's thighs rather than be fastened under the crotch of the undergarment. An advantage of the invention is that the pad 80 is not rigidly attached to the undergarment but may move somewhat with the movements of the wearer or with movement of the pad's cover material.

Figure 18:
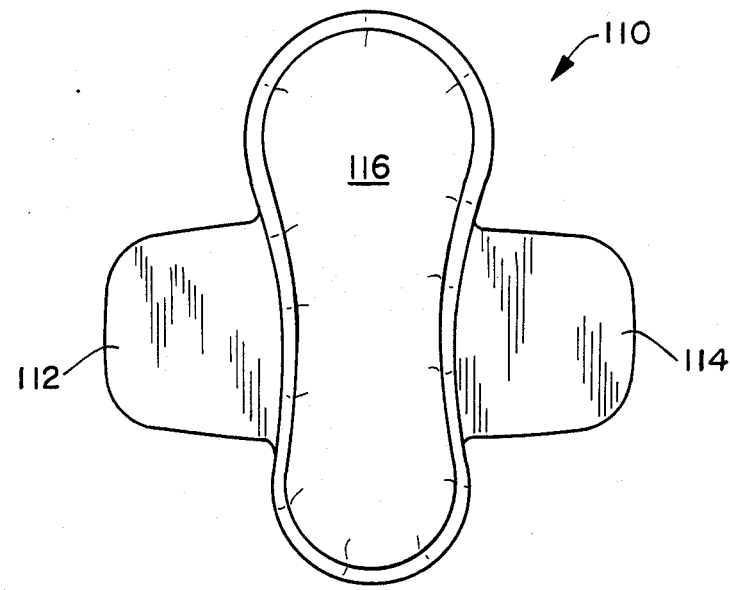
FIGS. 18 and 19 are top and bottom views of another embodiment of a pad in accordance with the invention.
Figure 19:
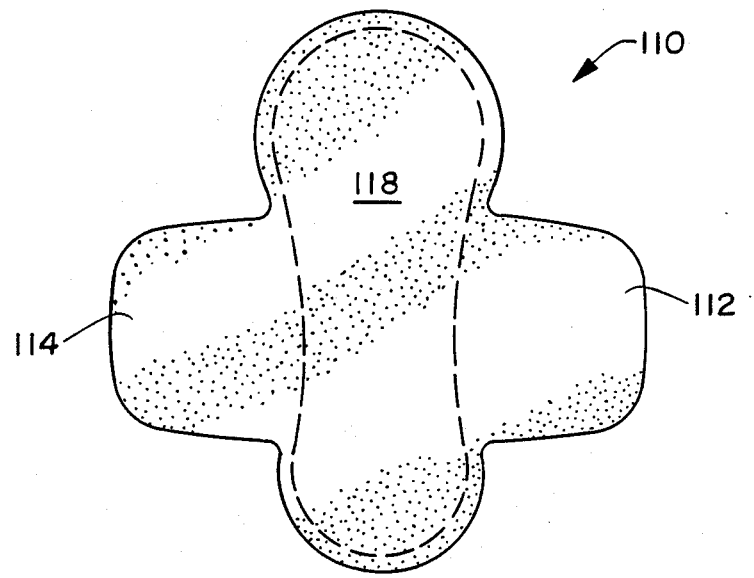

The pad 110 illustrated in FIGS. 18 and 19 is provided with wings 112 and 114. The wings 112 and 114 extend outward from an absorbent area 116 on the bodyside and from a back surface 118. Substantially the entire back surface 118 is provided with the skid-resistant coating as is substantially the entire area of wings 112 and 114. This pad 110 is designed so that the skid-resistant coating on the back surface 118 and on the wings 112 and 114 bears against the wearer's body and the wearer's undergarment will hold the pad 110 in place without the use of adhesives. As an alternative, it is possible that the wings 112 and 114 could be provided with adhesive on the back surface 118 such that they fasten to each other beneath the wearer's underpants.

As illustrated by the above drawings, the skid-resistant coating may be applied to any of a variety of catamenial pads and adult and children incontinence garments. Furthermore, the skid-resistant coating may be applied either to the bodyside of the pad or to the backside of the pad. Generally, the coating is applied to a large portion of the pad's back surface. However, depending on the pad's size and the anti-skid properties of the particular coating utilized it may be necessary to only coat a portion of the back surface of the pad.

The skid-resistant coating may be utilized either as the only garment placement system or in combination with a conventional garment attachment adhesive. For instance, a small area of garment attachment adhesive could be utilized in order to hold the pad in place while the undergarment was being raised and lowered, but with the skid-resistant coating serving as the primary positioning means for the pad as it was worn. This would result in lower cost as less garment attachment adhesive would be utilized and further would allow the pad to move somewhat with the body rather than being rigidly attached to the undergarment.

The materials suitable for the coating may be any latex or hot melt that has sufficient skid-resistant properties to hold a feminine or incontinence pad in place in an undergarment during use. The coating should present a generally smooth, pore-free and nonporous surface after application to the pad. The coefficient of friction of the coating material has been measured by a Davis Modified form of ASTM test No. D-1894. The D-1894 test calls for a sled wrapped with sponge rubber to be pulled across the test sample at 0.5 inches per minute. The modified Davis test involves wrapping the sled with test samples and pulling them across a Naugahyde sheet at 0.5 inches per minute. Using this test a coefficient of friction of greater than 1 has been found to be satisfactory. A Sheffield smoothness rating of greater than 200 has been found to be suitable. A preferred coefficient of friction is between 1 and 2.5 combined with a smoothness rating of between about 200 and 325.

The anti-skid coatings may be any suitable composition which generally fall into the following groups of materials that include those having adequate skid-resistant properties:

Ethylene vinyl acetate copolymers—could be applied as a hot melt or as a water based coating. Best candidates have at least 28% vinyl acetate Polyvinyl acetate—normally used in water-based emulsions Styrene-butadiene—applied in an emulsion or as a hot melt Cellulose acetate butyrate—normally hot melt coatings Ethyl cellulose—normally blended with a plasticizer and a resin and applied as a hot melt Acrylics—normally emulsion systems that are not blended Synthetic rubber hot melt—(Kraton ®) block copolymers having elastomeric and styrenic blocks, rubber, resin, plasticizer blends Other hot melts—polyethylenes (alone or blended); polyamides, etc.

Typical of such compositions are the ethylene-vinyl acetate copolymers, acrylic terpolymers of methacrylic acids, acrylic copolymers, ethylene-vinyl acetate/resin latex emulsions, ethylene-vinyl acetate hot-melt adhesives, synthetic rubber (block copolymers with elastomeric and styrenic components) hot melt adhesives, and polyvinyl acetate/resin emulsions. Such materials are available from H. B. Fuller Company, E. I. DuPont and Findley Adhesives, among others. Compositions of these types have found use as hot-melt and water-based coatings for barrier coatings for nonwovens and/or papers.

While it has been disclosed that the coating can be placed over a fluid-impermeable layer, it is also possible that the coating can be placed over a liquid-permeable layer that would become liquid-impermeable by the action of the coating. This would have the advantage that a low-cost scrim or nonwoven material could be used as the backing layer with the hot-melt or latex serving both the purpose of forming a fluid-impermeable backing layer when sealed to the fabric and forming a skid-resistant coating for pad positioning.

The above description has been intended to be illustrative rather than exhaustive of the possibilities of the invention. For instance, while not illustrated, the skid-resistant coatings could be utilized for the products intended for partial labial disposition such as U.S. Pat. No. 4,673,403—Lassen et al. The skid-resistant coatings could also cover a portion of the absorbent on the ends and/or edges of the bodyside of the pad.

While the invention has been described in connection with specific embodiments, it will be understood that the invention is not intended to be limited to those embodiments. On the contrary, the invention is intended to encompass all alternatives, modifications and variations as may be included within the spirit and scope of the appended claims.

We claim:

1. An absorbent article for absorbing fluid comprising an absorbent positioned between a bodyside layer and a backing layer and a nonadhesive, skid-resistant coating applied to at least one of said layers for facilitating positioning of said article relative to the anatomy of a user, said coating providing a dry surface having a coefficient of friction of greater than 1.0 and a Sheffield smoothness of greater than about 200.

2. The article of claim 1 wherein said coating is applied to said bodyside layer and directly contacts the body of the user.

3. The article of claim 2 wherein said coating is applied to said backing layer and provides resistance to movement of said article relative to an undergarment.

4. The article of claim 1 wherein said coating is applied to both of said layers for facilitating positioning said article to the anatomy of the user.

5. The article of claim 1 wherein said coating has a coefficient of friction of between about 1.0 and 2.5.

6. The article of claim 1 wherein said coating has a Sheffield smoothness rating of between about 200 and 325.

7. The article of claim 1 wherein said coating is selected from a group consisting of:
ethylene-vinyl acetate copolymers, polyvinylacetate, isobutylene, styrene-butylene, cellulose acetate butyrate, ethyl cellulose, acrylics, synthetic rubber hot melts or mixtures thereof.

8. An article for absorption of human exudate comprising an absorbent positioned between a bodyside layer and a backing layer, said structure having a pair of longitudinal sides with a pair of wings extending outward from the edges thereof a distance sufficient to extend beyond the edges of the crotch of an undergarment and a nonadhesive, skid-resistant coating applied to at least one of said layers for facilitating positioning of said article relative to the anatomy of a user, said coating having a coefficient of friction of greater than 1.0 and a Sheffield smoothness of greater than about 200.

9. The article of claim 8 wherein said coating is applied to said bodyside layer and directly contacts the body of the user.

10. The article of claim 8 wherein said coating is applied to said backing layer and provides resistance to movement of said article relative to an undergarment.

11. The article of claim 8 wherein said coating is applied to both of said layers for facilitating positioning said article to the anatomy of the user.

12. The article of claim 8 wherein said coating has a coefficient of friction of between about 1.0 and 2.5.

13. The article of claim 8 wherein said coating has a Sheffield smoothness rating of between about 200 and 325.

14. The article of claim 8 wherein said coating is selected from a group consisting of:
ethylene-vinyl acetate copolymers, polyvinylacetate, isobutylene, styrene-butylene, cellulose acetate butyrate, ethyl cellulose, acrylics, synthetic rubber hot melts or mixtures thereof.

15. The article of claim 8 wherein said coating is applied to a surface of each of said wings.

* * * * *